United States Patent
Gilles et al.

(10) Patent No.: US 8,110,190 B2
(45) Date of Patent: Feb. 7, 2012

(54) ANTI-IDIOTYPIC ANTIBODIES NEUTRALIZING THE INHIBITORY ACTIVITY OF AN INHIBITORY ANTIBODY DIRECTED AGAINST THE C1 DOMAIN OF FACTOR VIII

(76) Inventors: Jean-Guy Gilles, Brussels (BE); Marc G. Jacquemin, Sart-Bernard (BE); Jean-Marie Saint-Remy, Grez-Boiceau (BE); Christian Behrens, Palaiseau (FR)

( * ) Notice: Subject to any disclaimer, the term of this patent is extended or adjusted under 35 U.S.C. 154(b) by 866 days.

(21) Appl. No.: 11/844,331

(22) Filed: Aug. 23, 2007

(65) Prior Publication Data

US 2009/0263380 A1    Oct. 22, 2009

Related U.S. Application Data

(63) Continuation of application No. PCT/FR2007/000342, filed on Feb. 26, 2007.

(30) Foreign Application Priority Data

Feb. 24, 2006   (FR) ..................... 06 01633

(51) Int. Cl.
*A61K 39/395*   (2006.01)

(52) U.S. Cl. ............... 424/131.1; 424/133.1; 424/141.1; 424/145.1; 530/387.2; 530/387.3; 530/388.1; 435/327; 514/14.1

(58) Field of Classification Search .................. None
See application file for complete search history.

(56) References Cited

FOREIGN PATENT DOCUMENTS

EP      1388544 A1 *  2/2004
WO   WO 2005016455 A2 *  2/2005

OTHER PUBLICATIONS

Rudikoff et al., Proc Natl Acad Sci U S A. Mar. 1982;79(6):1979-83.*
Janeway et al., Immunobiology, 3rd edition, 1997, Garland Press, pp. 3:1 to 3:11.*
William E. Paul, M.D. ed., Fundamental Immunology, 3d ed. 1993, p. 242.*
Portolano et al., J Immunol., 1993, 150:880-887.*

* cited by examiner

*Primary Examiner* — Michael Szperka
(74) *Attorney, Agent, or Firm* — 24IP Law Group

(57) ABSTRACT

The present invention is related to a monoclonal anti-idiotypic antibody directed against a Factor VIII inhibitor antibody binding to the C1 domain of Factor VIII, as well as to a cell line producing this monoclonal anti-idiotypic antibody, to the use of this monoclonal anti-idiotypic antibody as medicament, and more particularly to the use thereof for manufacturing a medicament intended for the treatment of haemophilia A.

16 Claims, 4 Drawing Sheets

SEQUENCE LISTING

<160> NUMBER OF SEQ ID NOS: 18

<210> SEQ ID NO 1
<211> LENGTH: 424
<212> TYPE: DNA
<213> ORGANISM: Mus musculus -continued

<400> SEQUENCE: 1

```
atgggatgga gctggatctt tctcttcctg ttttcagtaa ctgcaggtgt ccactcccag      60
gtccagcttc agcagtctgg ggctgaactg gcaaaacctg gggcctcagt gaagatgtcc     120
tgcaaggctt ctggctacac ctttactacc tactggatgc actggataaa acagaggcct     180
ggacaggatc tggaatggat tggatacatt aatcctacct ctggttatac tgagtacaat     240
cagaacttca aggacaaggc acattgact gcagacaaat cctccagcac agcctacatg      300
caactgaaca gcctgacatc tgaggactct gcagtctatt tctgtgcaag atcgggggcc     360
tactataggt acgacgatgc tatggactcc tggggtcaag aacctcagt caccgtctcc      420 tcag                                                                   424
```

<210> SEQ ID NO 2
<211> LENGTH: 391
<212> TYPE: DNA
<213> ORGANISM: Mus musculus

<400> SEQUENCE: 2

```
atggatttc aggtgcagat tttcagcttc ctgctattca gtgcctcagt cataatgtcc        60
agaggacaaa ttgttctctc ccagtctcca gcaatcctgt ctgcatctcc aggggagaag     120
gtcacaatga cttgcagggc cagctcaagt gtaagttaca tgaactggta tcagcagaag     180
ccaggatcct cccccaaacc ctggatttat gccacatcca acctggcttc tggagtccct     240
gctcgcttca gtggcagtgg gtctgggacc tcttattctc tcacaatcag cagagtggag     300
gctgaagatg ctgccactta ttactgccag cagtggagta gtaacccacc catgctcacg     360
ttcggtgctg ggaccaagct ggagctgaaa c                                     391
```

<210> SEQ ID NO 3
<211> LENGTH: 141
<212> TYPE: PRT
<213> ORGANISM: Mus musculus

<400> SEQUENCE: 3

Met Gly Trp Ser Trp Ile Phe Leu Phe Leu Phe Ser Val Thr Ala Gly
 1               5                  10                  15

Val His Ser Gln Val Gln Leu Gln Gln Ser Gly Ala Glu Leu Ala Lys
            20                  25                  30

Pro Gly Ala Ser Val Lys Met Ser Cys Lys Ala Ser Gly Tyr Thr Phe
        35                  40                  45

Thr Thr Tyr Trp Met His Trp Ile Lys Gln Arg Pro Gly Gln Asp Leu
    50                  55                  60

Glu Trp Ile Gly Tyr Ile Asn Pro Thr Ser Gly Tyr Thr Glu Tyr Asn
65                  70                  75                  80

Gln Asn Phe Lys Asp Lys Ala Thr Leu Thr Ala Asp Lys Ser Ser Ser
                85                  90                  95

Thr Ala Tyr Met Gln Leu Asn Ser Leu Thr Ser Glu Asp Ser Ala Val
            100                 105                 110

Tyr Phe Cys Ala Arg Ser Gly Ala Tyr Tyr Arg Tyr Asp Asp Ala Met
        115                 120                 125

Asp Ser Trp Gly Gln Gly Thr Ser Val Thr Val Ser Ser
    130                 135                 140

<210> SEQ ID NO 4
<211> LENGTH: 130
<212> TYPE: PRT
<213> ORGANISM: Mus musculus

<400> SEQUENCE: 4

Met Asp Phe Gln Val Gln Ile Phe Ser Phe Leu Leu Phe Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met Asn Trp Tyr Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Ser Ser Asn Pro Pro Met Leu Thr Phe Gly Ala Gly Thr Lys Leu Glu
        115                 120                 125

Leu Lys
    130

<210> SEQ ID NO 5
<211> LENGTH: 421
<212> TYPE: DNA
<213> ORGANISM: Homo sapiens

<400> SEQUENCE: 5
atggactgga cctggaggtt cctctttgtg gtggcagcag ctgcaggtgt ccagtcccag    60
gtgcagctgg tgcagtctgg ggctgaggtg aagaagcccg gtcgtcggt gatggtctcc    120
tgcaaggctt ctggaggcac cttcagcagc tttggtatca gctgggtgcg acaggcccct    180
ggacaagggc ttgagtgggt gggagggatc atccctatct tggtacagc aaacaccgca    240
cggaacttcc agaatagagt caccattacc gcggacgaat tcacgagcac agcctacata    300
cgactgagga gcctgagatc tgaagatacg gccgtgtatt actgtgtcgg cggtcgagat    360
gcctacagct tgatggtttt tgatgtctgg ggccaaggga caatggtcac cgtctcttca    420
g                                                                    421

<210> SEQ ID NO 6
<211> LENGTH: 385
<212> TYPE: DNA
<213> ORGANISM: Homo sapiens

<400> SEQUENCE: 6
atggcatgga tccctctctt cctcggcgtc cttgtttact gcacaggatc cgtggcctcc    60
tctgggctga ctcagccaca ctcagtgtcc gtgtccccag acagacagc caacatcacc    120
tgctctagag ataagttggg tcataaattt gcttcctggt atcaacagaa gccaggccag    180
tccccctgctc ttctcatcta tcaagacagc aagcggccct cagggatccc tgagcgattc    240
tctggctcca actctgggaa cacagccact ctgaccatca gcgggaccca ggctatggat    300
gaggctgact attactgtca ggcgtgggac aacaccactg ccgtattcgg cggagggacc    360
aagttgacag tcctaagtca gccca                                          385

<210> SEQ ID NO 7
<211> LENGTH: 140
<212> TYPE: PRT

<213> ORGANISM: Homo sapiens

<400> SEQUENCE: 7

Met Asp Trp Thr Trp Arg Phe Leu Phe Val Val Ala Ala Ala Ala Gly
1               5                   10                  15

Val Gln Ser Gln Val Gln Leu Val Gln Ser Gly Ala Glu Val Lys Lys
            20                  25                  30

Pro Gly Ser Ser Val Met Val Ser Cys Lys Ala Ser Gly Gly Thr Phe
        35                  40                  45

Ser Ser Phe Gly Ile Ser Trp Val Arg Gln Ala Pro Gly Gln Gly Leu
    50                  55                  60

Glu Trp Val Gly Gly Ile Ile Pro Ile Phe Gly Thr Ala Asn Thr Ala
65                  70                  75                  80

Arg Asn Phe Gln Asn Arg Val Thr Ile Thr Ala Asp Glu Phe Thr Ser
                85                  90                  95

Thr Ala Tyr Ile Arg Leu Arg Ser Leu Arg Ser Glu Asp Thr Ala Val
            100                 105                 110

Tyr Tyr Cys Val Gly Gly Arg Asp Ala Tyr Ser Phe Asp Gly Phe Asp
        115                 120                 125

Val Trp Gly Gln Gly Thr Met Val Thr Val Ser Ser
    130                 135                 140

<210> SEQ ID NO 8
<211> LENGTH: 128
<212> TYPE: PRT
<213> ORGANISM: Homo sapiens

<400> SEQUENCE: 8

Met Ala Trp Ile Pro Leu Phe Leu Gly Val Leu Val Tyr Cys Thr Gly
1               5                   10                  15

Ser Val Ala Ser Ser Gly Leu Thr Gln Pro His Ser Val Ser Val Ser
            20                  25                  30

Pro Gly Gln Thr Ala Asn Ile Thr Cys Ser Arg Asp Lys Leu Gly His
        35                  40                  45

Lys Phe Ala Ser Trp Tyr Gln Gln Lys Pro Gly Gln Ser Pro Ala Leu
    50                  55                  60

Leu Ile Tyr Gln Asp Ser Lys Arg Pro Ser Gly Ile Pro Glu Arg Phe
65                  70                  75                  80

Ser Gly Ser Asn Ser Gly Asn Thr Ala Thr Leu Thr Ile Ser Gly Thr
                85                  90                  95

Gln Ala Met Asp Glu Ala Asp Tyr Tyr Cys Gln Ala Trp Asp Asn Thr
            100                 105                 110

Thr Ala Val Phe Gly Gly Gly Thr Lys Leu Thr Val Leu Ser Gln Pro
        115                 120                 125

<210> SEQ ID NO 9
<211> LENGTH: 10
<212> TYPE: PRT
<213> ORGANISM: Mus musculus

<400> SEQUENCE: 9

Gly Tyr Thr Phe Thr Thr Tyr Trp Met His
1               5                   10

<210> SEQ ID NO 10
<211> LENGTH: 17
<212> TYPE: PRT
<213> ORGANISM: Mus musculus

```
<400> SEQUENCE: 10

Tyr Ile Asn Pro Thr Ser Gly Tyr Thr Glu Tyr Asn Gln Asn Phe Lys
1               5                   10                  15

Asp

<210> SEQ ID NO 11
<211> LENGTH: 13
<212> TYPE: PRT
<213> ORGANISM: Mus musculus

<400> SEQUENCE: 11

Ser Gly Ala Tyr Tyr Arg Tyr Asp Asp Ala Met Asp Ser
1               5                   10

<210> SEQ ID NO 12
<211> LENGTH: 10
<212> TYPE: PRT
<213> ORGANISM: Mus musculus

<400> SEQUENCE: 12

Arg Ala Ser Ser Ser Val Ser Tyr Met Asn
1               5                   10

<210> SEQ ID NO 13
<211> LENGTH: 7
<212> TYPE: PRT
<213> ORGANISM: Mus musculus

<400> SEQUENCE: 13

Ala Thr Ser Asn Leu Ala Ser
1               5

<210> SEQ ID NO 14
<211> LENGTH: 11
<212> TYPE: PRT
<213> ORGANISM: Mus musculus

<400> SEQUENCE: 14

Gln Gln Trp Ser Ser Asn Pro Pro Met Leu Thr
1               5                   10

<210> SEQ ID NO 15
<211> LENGTH: 367
<212> TYPE: DNA
<213> ORGANISM: Mus musculus

<400> SEQUENCE: 15
caggtccagc ttcagcagtc tggggctgaa ctggcaaaac ctggggcctc agtgaagatg      60
tcctgcaagg cttctggcta caccttact  acctactgga tgcactggat aaaacagagg     120
cctggacagg atctggaatg gattggatac attaatccta cctctggtta tactgagtac     180
aatcagaact tcaaggacaa ggccacattg actgcagaca atcctccag cacagcctac      240
atgcaactga cagcctgac  atctgaggac tctgcagtct atttctgtgc aagatcgggg     300
gcctactata ggtacgacga tgctatggac tctgggggtc aaggaacctc agtcaccgtc     360
tcctcag                                                               367

<210> SEQ ID NO 16
<211> LENGTH: 325
<212> TYPE: DNA
<213> ORGANISM: mus musculus

<400> SEQUENCE: 16
```

```
caaattgttc tctcccagtc tccagcaatc ctgtctgcat ctccagggga gaaggtcaca    60
atgacttgca gggccagctc aagtgtaagt tacatgaact ggtatcagca gaagccagga   120
tcctccccca aaccctggat ttatgccaca tccaacctgg cttctggagt ccctgctcgc   180
ttcagtggca gtgggtctgg gacctcttat tctctcacaa tcagcagagt ggaggctgaa   240
gatgctgcca cttattactg ccagcagtgg agtagtaacc cacccatgct cacgttcggt   300
gctgggacca agctggagct gaaac                                         325
```

<210> SEQ ID NO 17
<211> LENGTH: 122
<212> TYPE: PRT
<213> ORGANISM: Mus musculus

<400> SEQUENCE: 17

```
Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Thr Tyr
            20                  25                  30

Trp Met His Trp Ile Lys Gln Arg Pro Gly Gln Asp Leu Glu Trp Ile
        35                  40                  45

Gly Tyr Ile Asn Pro Thr Ser Gly Tyr Thr Glu Tyr Asn Gln Asn Phe
    50                  55                  60

Lys Asp Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Ala Arg Ser Gly Ala Tyr Tyr Arg Tyr Asp Asp Ala Met Asp Ser Trp
            100                 105                 110

Gly Gln Gly Thr Ser Val Thr Val Ser Ser
        115                 120
```

<210> SEQ ID NO 18
<211> LENGTH: 108
<212> TYPE: PRT
<213> ORGANISM: Mus musculus

<400> SEQUENCE: 18

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

Asn Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asn Pro Pro Met
                85                  90                  95

Leu Thr Phe Gly Ala Gly Thr Lys Leu Glu Leu Lys
            100                 105
```

ANTI-IDIOTYPIC ANTIBODIES NEUTRALIZING THE INHIBITORY ACTIVITY OF AN INHIBITORY ANTIBODY DIRECTED AGAINST THE C1 DOMAIN OF FACTOR VIII

This application claims priority under 35 U.S.C. §119 to French Patent Application No. 06 01633, filed Feb. 24, 2006, and under 35 U.S.C. §120 as a Continuation to PCT/FR2007/000342, filed Feb. 26, 2007, the contents of both of which are incorporated by reference herein in their entireties. The Sequence Listing electronically filed herewith is also hereby incorporated by reference in its entirety (File Name: 028-019_Seq_List_Copy_1; File Size: 12 KB; Date Created: Aug. 23, 2007).

BACKGROUND OF THE INVENTION

1. Field of the Invention

The present invention is related to a monoclonal anti-idiotypic antibody directed against a Factor VIII inhibitory antibody which binds to the C1 domain of Factor VIII, as well as to a cell line producing this monoclonal anti-idiotypic antibody, to the use of this monoclonal anti-idiotypic antibody as medicament, and more particularly, to the use thereof for manufacturing a medicament for the treatment of haemophilia A.

2. Brief Description of the Related Art

Haemophilia A is a hereditary disease linked to an anomaly of chromosome X, which displays itself in the affected person by an inability to coagulate. This disease is the result of mutations on the gene of a protein involved in coagulation, the Factor VIII (FVIII) protein, which determine either a total absence of Factor VIII in the blood, or a partial deficit thereof.

Haemophilia A is the most common of insufficiencies affecting blood coagulation: in France 1 male in 5000 is affected, which represents 80% of patients suffering from haemophilia. The other type of haemophilia, haemophilia B, affects 20% of patients suffering from haemophilia; it is caused by a deficiency in an other clotting factor, known as Factor IX.

Present treatment of haemophilia (type A or B) consists of intravenous administration of the deficient or absent clotting factor. In France, Factor VIII for the treatment of haemophiliacs is available in form of blood derived medicaments provided by the Laboratoire Français du Fractionnement et des Biotechnologies (LFB) or by international pharmaceutical laboratories, as well as in form of recombinant medicaments prepared by genetic engineering methods. Effectively, the DNA coding Factor VIII has been isolated and expressed in mammalian cells (Wood et al., Nature (1984) 312: 330-337), and its amino acid sequence was deduced from cDNA.

Secreted Factor VIII (FVIII) is a glycoprotein with a molecular weight of 300 Kda (2332 amino acids), and plays a key role in the activation of intrinsic coagulation pathway. Inactive FVIII consists of six regions: A1 (residues 1-372), A2 (residues 373-740), B (residues 741-1648), A3 (residues 1690-2019), C1 (residues 2020-2172) and C2 (residues 2173-2332), from the N-terminal extremity to the C-terminal extremity. After being secreted, FVIII interacts with the von Willebrand Factor (vWF), which protects the FVIII against plasma proteases. FVIII dissociates from vWF upon cleavage by thrombin. This cleavage results in the elimination of the B domain and the formation of a heterodimer. FVIII circulates in plasma in this form. This heterodimer consists of a heavy chain (A1, A2) and of a light chain (A3, C1, C2).

When FVIII is infused to a haemophiliac patient, it binds to the von Willebrand Factor in the blood circulation of the patient. Activated Factor VIII acts as a co-factor of activated Factor IX, accelerating the conversion of Factor X into activated Factor X. Activated Factor X converts prothrombin into thrombin. Then the thrombin converts fibrinogen into fibrin, and clotting occurs.

The major problem encountered with Factor VIII administration is the appearance of antibodies directed against Factor VIII in the patient, referred to as <<inhibiting antibodies>>. These antibodies neutralize the procoagulant activity of Factor VIII, which is inactivated as soon as infused. Thus, the administered clotting factor is destroyed before bleeding can be stopped, which leads to a serious complication thus causing the treatment to be ineffective. Further, some genetically non-haemophiliac patients may develop inhibitors against endogenous Factor VIII: this is called acquired haemophilia.

Studies have shown that the anti-Factor VIII immune response is of the polyclonal IgG type belonging mostly to the IgG4 and IgG1 sub-class, and more rarely to IgG2. The IgG3 subclass is never represented. The light chain is often of Kappa type. The overrepresentation of IgG4 is more pronounced with haemophiliacs having a long-term established inhibitor. The C2 and A2 domains of the FVIII molecule are the favoured targets of the immune response although, in some cases, antibodies directed against the A3 domain are detected. When plasma of haemophiliac patients is passed through an immunoadsorption column with immobilized FVIII, it is possible to purify total anti-FVIII antibodies. The recovered amounts are often higher than 100 µg per 10 mg of total IgGs (Gilles J G et al. (1993) Blood; 82: 2452-2461). An animal model has been developed to study the formation of inhibitors of Factor VIII; rats immunized with human recombinant Factor VIII show a rapid immune response of the polyclonal type (Jarvis et al., Thromb Haemost. 1996 February; 75(2):318-25). The mechanisms by which anti-Factor VIII antibodies interfere with function of Factor VIII are numerous, and include interference with the proteolytic cleavage of Factor VIII and with the interaction of Factor VIII with different partners, such as von Willebrand Factor (vWF), phospholipids (PL), Factor IX, activated Factor X (FXa) or APC (Activated Protein C).

Several treatments allowing attenuation of the consequences of this immune response are available, such as for example treatments involving desmopressin, which is a synthetic hormone stimulating the production of Factor VIII, coagulation promoting agents, such as concentrates of prothrombin complexes or concentrates of activated prothrombin complexes, recombinant Factor VIIa, plasmapheresis and infusions of large or intermediary amounts of Factor VIII. Nevertheless, these methods are very expensive and of low efficacy.

Because of the complexity of the in vivo analysis of this immune polyclonal response, monoclonal antibodies directed against certain domains of Factor VIII have been isolated by some research teams. Thus, a human monoclonal antibody of the IgG4kappa type, LE2E9, has been isolated. This antibody is directed against the C1 domain of Factor VIII and inhibits the cofactor activity of Factor VIII and its binding to the von Willebrand Factor (Jacquemin et al., (2000) Blood 95:156-163). In the same way, a human monoclonal antibody directed against the C2 domain of Factor VIII, referred to as BO2C11 (IgG4kappa), produced from a library of memory B cells of a patient suffering from haemophilia A with inhibitors, has been isolated (Jacquemin et al., Blood 1998 Jul. 15; 92 (2):496-506). BO2C11 recognizes the C2 domain of Factor VIII, and inhibits its binding to von Willebrand Factor and to phospholipids. It completely inhibits the procoagulation activity of native and activated Factor VIII. A further example of monoclonal antibody is the BOIIB2 antibody directed against the A2 domain of Factor VIII. The BOIIB2 antibody inhibits 99% of Factor VIII activity. By binding to the A2 domain, it can interfere with and inhibit the binding of FIXa, which contains a low affinity binding site within this region of FVIII, and thus inhibits the enzyme activity of FIXa. The second conceivable way of action is its interference with the equilibrium between the heterodimeric form (A2:A1 and A3:C1:C2) of FVIII and the heterotrimeric form (A2 and A1 and A3:C1:C2) of FVIII by accelerating the dissociation of the A2 domain of these complexes, rendering them non-functional. (Ananyeva N M et al., (2004) Blood Coagul Fibrinolysis. Mar. 15(2):109-24. Review).

With the aid of these new tools, a further, more recent strategic struggle against the Factor VIII inhibitor antibodies has considered administering anti-idiotypic antibodies (antibodies having the ability to interact with the variable region of other antibodies) neutralizing the inhibitor antibodies (Saint-Rémy J M et al., (1999) Vox Sang; 77 (suppl 1): 21-24). A mouse anti-idiotypic antibody, known as 14C12, disclosed in the document WO 2004/014955, neutralizes in vivo, in a dose-dependent manner, the inhibitory properties of the anti-Factor VIII target antibody (monoclonal antibody BO2C11), which is directed against the C2 domain of Factor VIII. The anti-Factor VIII immune response being polyclonal, mouse anti-idiotypic antibodies directed against the A2 domain of Factor VIII have also been developed (and described in the patent application FR 05 08320). The A2 domain is a domain of 43 kD, the function of which is not well known but it has been demonstrated that inhibitory antibodies directed against the A2 domain of Factor VIII inhibit the function of Factor VIIIa by inhibiting the conversion of the complex FXase/FX in the transition state (Lollar et al., J Clin Invest. 1994 June; 93(6):2497-504, Fay et al., J Biol. Chem. 1996; 271(11): 6027-6032).

However, the immune response directed against Factor VIII is polyclonal, and, therefore, implies that inhibitory antibodies are directed against domains different from the A2 and C2 domains. Indeed, even if the study of epitopic specificities of anti-Factor VIII antibodies has shown that the majority of the inhibitors recognize limited zones of the Factor VIII molecule, located on the A2 domain of the heavy chain and/or on the C2 domain of the light chain, other epitopes are sometimes recognized. Indeed, some plasmas from patients contain antibodies capable to bind to the C1 domain of the light chain of Factor VIII (Moreau et al., 2000; 95(11):3435-441; Jacquemin et al., 2000; 95(1):156-162).

Thus, there is always a need for further tools enabling neutralization of other Factor VIII inhibitory antibodies directed against other domains of Factor VIII, in order to more completely neutralize the anti-Factor VIII polyclonal responses of haemophiliac patients.

Thus, the Applicant has attempted to develop a novel tool for treating haemophilia A enabling neutralization of inhibitory antibodies directed against the C1 domain of Factor VIII.

DETAILED DESCRIPTION OF EXEMPLARY EMBODIMENTS

Figure 1:
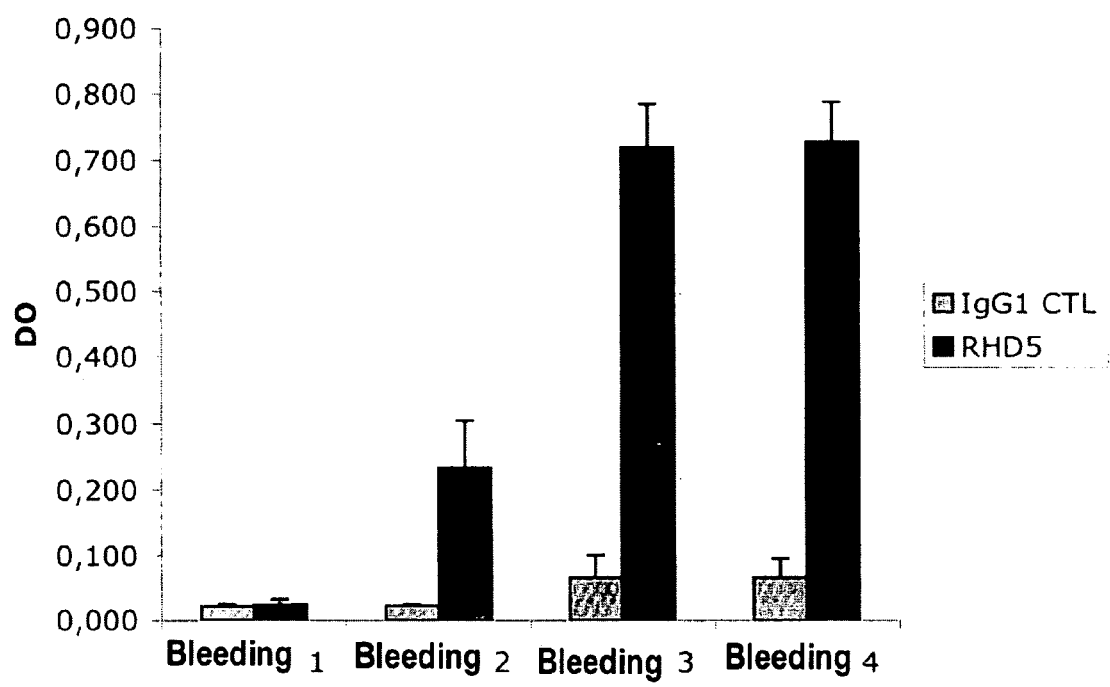
FIG. 1: increase (mean value) for the 4 mice in the binding of anti-idiotypic antibodies to RHD5.

Thus, a first aspect of the invention relates to a monoclonal anti-idiotypic antibody directed against a Factor VIII human inhibitory antibody, the inhibitory antibody being directed against the C1 domain of Factor VIII, this anti-idiotypic antibody having at least one CDR region (Complementarity Determining Region) of each of the light chains of said antibody, in which the peptide sequence has at least 70% identity to a sequence selected from the sequences SEQ ID NO: 12, SEQ ID NO: 13, SEQ ID NO: 14 and at least one CDR region of each of the heavy chains of said antibody, in which the peptide sequence has at least 70% identity to a sequence selected from the sequences SEQ ID NO: 9, SEQ ID NO: 10, SEQ ID NO: 11.

The concerned CDR regions are the CDR1 and/or CDR2 and/or CDR3 regions.

The sequences SEQ ID NO: 9, SEQ ID NO: 10, SEQ ID NO: 11, SEQ ID NO: 12, SEQ ID NO: 13 and SEQ ID NO: 14, are defined according to Kabat [Kabat et al., "Sequences of Proteins of Immunological Interest", NIH Publication, 91-3242 (1991)].

In a particularly advantageous embodiment, the identity with each of the above-mentioned sequences is at least 80%, preferably at least 90%, 95%, 99%, and more preferably 100%. The percentage of identity is calculated by aligning the two sequences to be compared and by counting the number of positions having an identical amino acid, this number being divided by the total number of amino acids of the sequence. In any case, these sequence differences do not affect at all either the affinity of the monoclonal antibody for its target, or its functionality.

<<Inhibitory antibodies>> or <<inhibitors>> of Factor VIII refers to antibodies which inhibit all or a part of the procoagulant activity of Factor VIII, namely by binding thereto, and particularly an anti-Factor VIII antibody the epitope of which is located on Factor VIII. Advantageously, the antibody of the invention has the ability to neutralize at least 20%, advantageously at least 30%, advantageously at least 40%, advantageously at least 50%, advantageously at least 60%, and in an even more advantageous way, at least 70%, 80%, 90%, 99% or 100% of the coagulation inhibitory activity of inhibitory antibodies directed against the C1 domain of Factor VIII, which are the targets of the anti-idiotypic monoclonal antibodies of the invention. This ability to neutralize the coagulation inhibitory activity of inhibitory antibodies can be determined by measuring the activity of Factor VIII in the presence of an inhibitory antibody and of an anti-idiotypic antibody in an assay such as the <<Factor VIII chromogen test>> (Jacquemin et al. (1998) Blood 92. 494-506).

The expression <<anti-idiotypic antibody>> refers to an antibody directed against the variable region of the target inhibitory antibodies. In a particular aspect of the invention, the anti-idiotypic antibody of the invention is directed against inhibitory antibodies, of which the variable domain of the heavy chain of said antibody is related to the germ line DP-10. Such inhibitory antibodies can be obtained from humans (for example from serum of patients containing inhibitory antibodies) or other animal species such as mouse, horse, goat, non-human primates, taken from a non-limiting list, by immunization with Factor VIII or fragments derived from Factor VIII, and more particularly with a fragment comprising all or a part of the C1 domain.

Advantageously, the target inhibitory antibody of the anti-idiotypic antibody of the invention recognizes the C1 domain in its native configuration. Advantageously, the target inhibitory antibody of the anti-idiotypic antibody of the invention does not recognize the same domain being a R2150H mutation.

The monoclonal anti-idiotypic antibody of the invention can be of human or animal origin. In addition, it can be obtained using a variety of different methods. For example, cells producing anti-idiotypic antibodies can be obtained from peripheral blood lymphocytes of patients having anti-Factor VIII inhibitory antibodies or from healthy persons. These cells can be immortalized by use of techniques well known to those skilled in the art and selected with regard to the ability of the produced anti-idiotypic antibodies to neutralize inhibitory antibodies directed against Factor VIII. A further method for producing the monoclonal anti-idiotypic antibody of the invention is through the immunization of animals, advantageously mice, by injection of Factor VIII inhibitory antibodies directed against the C1 domain of Factor VIII, then by fusion of spleen lymphocytes with a myeloma cell line, advantageously mouse myeloma, followed by the identification and the cloning of cell cultures producing the anti-idiotypic antibodies directed against the Factor VIII inhibitory antibodies.

In a preferred embodiment of the invention, each CDR region of the light chains of the anti-idiotypic antibody of the invention contains a peptide sequence having at least 70% identity with the sequences respectively identified as SEQ ID NO: 12, SEQ ID NO: 13 and SEQ ID NO: 14, and each CDR region of each of the heavy chains of said antibody contains a peptide sequence having at least 70% identity with the sequences respectively identified as SEQ ID NO: 9, SEQ ID NO: 10 and SEQ ID NO: 11.

Thus, the CDR1 region of each of the light chains of the antibody of the invention contains a peptide sequence having at least 70% identity to the sequence SEQ ID NO: 12, the latter having the amino acid sequence Arg Ala Ser Ser Ser Val Ser Tyr Met Asn, the CDR2 region of each of the light chains of the antibody of the invention contains a peptide sequence having at least 70% identity to the sequence SEQ ID NO: 13, the latter having the amino acid sequence Ala Thr Ser Asn Leu Ala Ser, the CDR3 region of each of the light chains of the antibody of the invention contains a peptide sequence having at least 70% identity to the sequence SEQ ID NO: 14, the latter having the amino acid sequence Gln Gln Trp Ser Ser Asn Pro Pro Met Leu Thr, and the CDR1 region of each of the heavy chains of the antibody of the invention contains a peptide sequence having at least 70% identity to the sequence SEQ ID NO 9, the latter having the amino acid sequence Gly Tyr Thr Phe Thr Thr Tyr Trp Met His, the CDR2 region of each of the heavy chains of the antibody of the invention contains a peptide sequence having at least 70% identity to the sequence SEQ ID NO: 10, the latter having the amino acid sequence Tyr Ile Asn Pro Thr Ser Gly Tyr Thr Glu Tyr Asn Gln Asn Phe Lys Asp, and the CDR3 region of each of the heavy chains of the antibody of the invention contains a peptide sequence having at least 70% identity to the sequence SEQ ID NO: 11, the latter having the amino acid sequence Ser Gly Ala Tyr Tyr Arg Tyr Asp Asp Ala Met Asp Ser. In a particularly advantageous way, the identity to each of the above-mentioned sequences is at least 80%, preferably at least 90%, 95%, 99% and more preferably 100%.

Advantageously, the variable region of each of the light chains of the monoclonal anti-idiotypic antibody of the invention is coded by a nucleic acid sequence having at least 70% identity to the nucleic acid sequence SEQ ID NO: 16, the latter having the following nucleic acid sequence:

caaattgttc tctcccagtc tccagcaatc ctgtctgcat ctccagggga gaaggtcaca atgacttgca gggccagctc aagtgtaagt tacatgaact ggtatcagca gaagccagga tcctccccca aaccctggat ttatgccaca tccaacctgg cttctggagt ccctgctcgc ttcagtggca gtgggtctgg gac-ctcttat tctctcacaa tcagcagagt ggaggctgaa gatgctgcca cttattactg ccagcagtgg agtagtaacc cacccatgct cacgttcggt gctgggacca agctggagct gaaac, and the variable region of each of the heavy chains of the monoclonal anti-idiotypic antibody is coded by a nucleic acid sequence having at least 70% identity to the nucleic acid sequence SEQ ID NO: 15, the latter having the following nucleic acid sequence:

```
caggtccagc ttcagcagtc tggggctgaa ctggcaaaac
ctggggcctc agtgaagatg tcctgcaagg cttctggcta
cacctttact acctactgga tgcactggat aaaacagagg
cctggacagg atctggaatg gattggatac attaatccta
cctctggtta tactgagtac aatcagaact tcaaggacaa
ggccacattg actgcagaca aatcctccag cacagcctac
atgcaactga acagcctgac atctgaggac tctgcagtct
atttctgtgc aagatcgggg gcctactata ggtacgacga
tgctatggac tcctggggtc aaggaacctc agtcaccgtc
tcctcag.
```

For the purposes of the invention, a signal peptide can be added to sequences SEQ ID NO: 15 and SEQ ID NO: 16 to yield respectively, for example, the sequences SEQ ID NO: 1 and SEQ ID NO: 2, wherein neither the activity nor the specificity of the antibody of the invention are affected by such a signal peptide.

The sequence of SEQ ID NO: 1 correspond to the following nucleic acid sequence:

```
atgggatgga gctggatctt tctcttcctg ttttcagtaa
ctgcaggtgt ccacteccag gtccagcttc agcagtctgg
ggctgaactg gcaaaacctg gggcctcagt gaagatgtcc
tgcaaggctt ctggctacac ctttactacc tactggatgc
actggataaa acagaggcct ggacaggatc tggaatggat
tggatacatt aatcctacct ctggttatac tgagtacaat
cagaacttca aggacaaggc cacattgact gcagacaaat
cctccagcac agcctacatg caactgaaca gcctgacatc
tgaggactct gcagtctatt tctgtgcaag atcgggggcc
tactataggt acgacgatgc tatggactcc tggggtcaag
gaacctcagt caccgtctcc tcag.
```

The sequence of SEQ ID NO: 2 correspond to the following nucleic acid sequence:

```
atggattttc aggtgcagat tttcagcttc ctgctattca
gtgcctcagt cataatgtcc agaggacaaa ttgttctctc
```

```
ccagtctcca gcaatcctgt ctgcatctcc aggggagaag gtcacaatga cttgcagggc cagctcaagt gtaagttaca tgaactggta tcagcagaag ccaggatect cccccaaacc ctggatttat gccacatcca acctggcttc tggagtccct gctcgcttca gtggcagtgg gtctgggacc tcttattctc tcacaatcag cagagtggag gctgaagatg ctgccactta ttactgccag cagtggagta gtaacccacc catgctcacg ttcggtgctg ggaccaagct ggagctgaaa c.
```

In a particularly advantageous way, the sequence identity is at least 80%, and preferably from at least 95 to 99%. The percentage of identity is calculated by alignment of 2 sequences to be compared and by counting the number of positions containing an identical nucleotide, this number is divided by the total number of nucleotides of the sequence. Genetic code degeneration leads to the fact that the same amino acid can be coded by several triplets of different nucleotides. In any case, neither the affinity of the monoclonal antibody for its target nor its ability to neutralize the inhibitory activity of the target inhibitory antibodies are at all affected by these sequence differences.

In a preferred aspect of the invention, the variable region of each of the light chains of the monoclonal anti-idiotypic antibody is coded by the nucleic acid sequence SEQ ID NO: 16, and the variable region of each of the heavy chains of the monoclonal anti-idiotypic antibody is coded by the nucleic acid sequence SEQ ID NO: 15.

In an advantageous manner, the peptide sequence of each of the variable regions of the light chains of the antibody of the invention is a sequence having at least 70% identity, and advantageously at least 80% or 90%, and yet more advantageously at least 99% identity to the sequence SEQ ID NO: 18, the latter having the following amino acid sequence:

```
Gln Ile Val Leu Ser Gln Ser Pro Ala Ile Leu Ser

Ala Ser Pro Gly Glu Lys Val Thr Met Thr Cys Arg

Ala Ser Ser Ser Val Ser Tyr Met Asn Trp Tyr Gln

Gln Lys Pro Gly Ser Ser Pro Lys Pro Trp Ile Tyr

Ala Thr Ser Asn Leu Ala Ser Gly Val Pro Ala Arg

Phe Ser Gly Ser Gly Ser Gly Thr Ser Tyr Ser Leu

Thr Ile Ser Arg Val Glu Ala Glu Asp Ala Ala Thr

Tyr Tyr Cys Gln Gln Trp Ser Ser Asn Pro Pro Met

Leu Thr Phe Gly Ala Gly Thr Lys Leu Glu Leu Lys.
```

For the purposes of the invention, a signal peptide can be added to the sequences SEQ ID NO 17 and SEQ ID NO: 18 in order to yield, for example, respectively, the sequences SEQ ID NO: 3 and SEQ ID NO: 4, neither the activity nor the specificity of the antibody of the invention are affected at by such a signal peptide.

Advantageously, the peptide sequence of each of the variable regions of the heavy chains of the antibody of the invention is a sequence having at least 70% identity, and advantageously at least 80% or 90%, and yet more advantageously at least 99% identity to the sequence SEQ ID NO: 3, the latter having the following amino acid sequence:

```
Met Gly Trp Ser Trp Ile Phe Leu Phe Leu Phe Ser

Val Thr Ala Gly Val His Ser Gln Val Gln Leu Gln

Gln Ser Gly Ala Glu Leu Ala Lys Pro Gly Ala Ser

Val Lys Met Ser Cys Lys Ala Ser Gly Tyr Thr Phe

Thr Thr Tyr Trp Met His Trp Ile Lys Gln Arg Pro

Gly Gln Asp Leu Glu Trp Ile Gly Tyr Ile Asn Pro

Thr Ser Gly Tyr Thr Glu Tyr Asn Gln Asn Phe Lys

Asp Lys Ala Thr Leu Thr Ala Asp Lys Ser Ser Ser

Thr Ala Tyr Met Gln Leu Asn Ser Leu Thr Ser Glu

Asp Ser Ala Val Tyr Phe Cys Ala Arg Ser Gly Ala

Tyr Tyr Arg Tyr Asp Asp Ala Met Asp Ser Trp Gly

Gln Gly Thr Ser Val Thr Val Ser Ser.
```

In a particularly advantageous manner, the peptide sequence of each of the light chains of the antibody of the invention is a sequence having at least 70% identity, and advantageously at least 80% or 90%, and yet more advantageously at least 99% identity to the sequence SEQ ID NO: 4, and the peptide sequence of each of the heavy chains of the antibody of the invention is a sequence having at least 70% identity, and advantageously at least 80% or 90%, and yet more advantageously, at least 99% identity to the sequence SEQ ID NO: 3.

Preferably, the peptide sequence of each of the light chains of the antibody of the invention is the sequence SEQ ID NO: 4, the latter having the following amino acid sequence:

```
Met Asp Phe Gln Val Gln Ile Phe Ser Phe Leu Leu

Phe Ser Ala Ser Val Ile Met Ser Arg Gly Gln Ile

Val Leu Ser Gln Ser Pro Ala Ile Leu Ser Ala Ser

Pro Gly Glu Lys Val Thr Met Thr Cys Arg Ala Ser

Ser Ser Val Ser Tyr Met Asn Trp Tyr Gln Gln Lys

Pro Gly Ser Ser Pro Lys Pro Trp Ile Tyr Ala Thr

Ser Asn Leu Ala Ser Gly Val Pro Ala Arg Phe Ser

Gly Ser Gly Ser Gly Thr Ser Tyr Ser Leu Thr Ile

Ser Arg Val Glu Ala Glu Asp Ala Ala Thr Tyr Tyr

Cys Gln Gln Trp Ser Ser Asn Pro Pro Met Leu Thr

Phe Gly Ala Gly Thr Lys Leu Glu Leu Lys.
```

Preferably, the peptide sequence of each of the light chains of the antibody of the invention is the sequence SEQ ID NO: 3.

The peptide sequence deduced from the sequence SEQ ID NO: 16 is the sequence SEQ ID NO: 18, and the peptide sequence deduced from the sequence SEQ ID NO: 15 is the sequence SEQ ID NO: 17, the latter having the following amino acid sequence:

```
Gln Val Gln Leu Gln Gln Ser Gly Ala Glu Leu Ala

Lys Pro Gly Ala Ser Val Lys Met Ser Cys Lys Ala
```

-continued

```
Ser Gly Tyr Thr Phe Thr Thr Tyr Trp Met His Trp

Ile Lys Gln Arg Pro Gly Gln Asp Leu Glu Trp Ile

Gly Tyr Ile Asn Pro Thr Ser Gly Tyr Thr Glu Tyr

Asn Gln Asn Phe Lys Asp Lys Ala Thr Leu Thr Ala

Asp Lys Ser Ser Ser Thr Ala Tyr Met Gln Leu Asn

Ser Leu Thr Ser Glu Asp Ser Ala Val Tyr Phe Cys

Ala Arg Ser Gly Ala Tyr Tyr Arg Tyr Asp Asp Ala

Met Asp Ser Trp Gly Gln Gly Thr Ser Val Thr Val

Ser Ser.
```

Preferably, the variable region of each of the light chains of the monoclonal anti-idiotypic antibody of the invention has the peptide sequence SEQ ID NO: 18, and the variable region of each of the heavy chains of the monoclonal anti-idiotypic antibody of the invention has the peptide sequence SEQ ID NO: 17.

In a preferred manner, the target inhibitory antibody of the anti-idiotypic antibody of the invention is the antibody RHD5 deposited at the Belgian Co-ordinated Collections of Micro-organisms/Plasmid Collection (BCCM/LMBP), Laboratorium voor Moleculaire Biologie, University of Ghent, Technologiepark 297, B-9052 Zwijnaarede, Belgium, in August 2004, by the Collen Research Foundation, under the accession number LMBP 6165CB. This antibody, as well as its nucleotide and peptide sequences are described in the patent application WO 2005/016455. The antibody RHD5 is a human monoclonal IgG1 antibody directed against the C1 domain of Factor VIII produced initially from lymphocytes of a patient suffering from haemophilia A, namely an acquired severe haemophilia A with a high level of inhibitors. This antibody belongs to the sub-class IgG1, and originates from the germ line DP-10. The epitope recognized by said antibody on Factor VIII is the C1 domain in its native configuration, but not the same domain with a R2150H mutation. The antibody RHD5 can inhibit up to 98% of Factor VIII activity.

The antibody of the invention refers also to any modified antibody having the features of the invention, in which one or more amino acid(s) have been substituted or deleted. Such a substitution or deletion can be located on any position in the molecule. In the case where several amino acids have been substituted or deleted, any combination of substitution or deletion can be considered. Such sequence modifications of the variable regions of the antibody of the invention can be carried out in order to increase the number of residues likely to come into contact with the anti-idiotypic antibody of the invention and with the target inhibitor antibody.

In one embodiment of the invention, the anti-idiotypic antibody is a mouse antibody.

Advantageously, this mouse monoclonal anti-idiotypic antibody is a IgG1kappa.

Preferably, the monoclonal antibody of the invention is a chimeric antibody. By the expression <<Chimeric antibody>> it is to be understood that it refers to an antibody in which the variable regions of the light chains and of the heavy chains belong to a different species than the constant regions of the light chains and of the heavy chains. Thus, the antibody of the invention, also contains the constant regions of light and heavy chains belonging to a non-murine species. In this regard, all non-murine mammalian families and species are capable of being used, and in particular, for example, man, monkey, muridae (except the mouse), suidae, bovidae, equidae, felidae, canidae, as well as birds.

The chimeric antibodies of the invention can be constructed using standard techniques for recombinant DNA, well known by those skilled in the art, and more particularly through the use of the <<chimeric>> antibody construction techniques described, for example by Morrison et al., Proc. Natl. Acad. Sci. U.S.A., 81. pp. 6851-55 (1984), where use is made of recombinant DNA technology to replace the constant region of a heavy chain and/or the constant region of a light chain of an antibody originating from a non-human mammal with the corresponding regions of a human immunoglobulin.

In a particular aspect of the invention, the antibody of the invention is a human hybrid antibody, that is to say a chimeric antibody, the constant part of which is human. This embodiment of the invention enables a reduction in the immunogenicity of the antibody in humans, and thereby improves its efficacy upon therapeutic administration to man.

Advantageously, the antibody of the invention is a humanized antibody. Such an antibody can be obtained by association of one or more CDR region(s) (Complementarity Determining Region) of a monoclonal antibody of a non-human species with human framework regions (highly conserved regions of variable regions, known as frameworks), such a manufacturing process being taught in the state of the art (Jones et al., Nature (1986) 321:522 Riechmann et al., Nature (1988) 332:323). Such a humanized antibody directed against the variable domain of inhibitory antibodies recognizing the C1 domain of FVIII can contain human framework regions and one or more CDR regions of the sequences SEQ ID NO: 9, SEQ ID NO: 10, SEQ ID NO: 11, SEQ ID NO: 12, SEQ ID NO: 13, SEQ ID NO: 14. A particular humanized antibody of the invention is a humanized antibody directed against the variable domain of inhibitory antibodies recognizing the C1 domain of FVIII, the CDR regions of which are regions of sequence SEQ ID NO: 9, SEQ ID NO: 10, SEQ ID NO: 11, SEQ ID NO: 12, SEQ ID NO: 13, SEQ ID NO: 14.

In an advantageous way, the monoclonal anti-idiotypic antibody of the invention is the antibody 18B6 produced by the hybridoma 18B6 deposited under the registration number CNCM I-3559, on Jan. 24, 2006, at the Collection Nationale de Cultures de Microorganismes (CNCM, 25 rue du Docteur Roux, 75724 Paris Cedex 15). The variable region of each of the light chains of the monoclonal anti-idiotypic antibody 18B6 is coded by the nucleic acid sequence SEQ ID NO: 16, and the variable region of each of the heavy chains of the monoclonal anti-idiotypic antibody 18B6 is coded by the nucleic acid sequence SEQ ID NO: 15. The method for obtaining the hybridoma 18B6 is described in the <<Examples>> section of the present document.

The monoclonal anti-idiotypic antibody of the invention refers also to any antibody comprising fragments of the antibody 18B6, and more particularly any antibody comprising the variable region of the light chain and/or the variable region of the heavy chain of the antibody 18B6, or any fragment of the variable region of the light chain and/or the variable region of the heavy chain of the antibody 18B6. By the expression <<Fragments>>, it is meant a F(ab')2 fragment or a Fab' fragment or a Fab fragment or a CDR region or any modified version of any of these fragments or region.

In a particular embodiment of the invention, the monoclonal anti-idiotypic antibody of the invention is a F(ab')2 fragment or a Fab' fragment or a Fab fragment or a CDR region or any modified version of any of these fragments or region. The enzymatic digestion of immunoglobulins with papain generates 2 identical fragments called <<Fab fragment>> (Fragment Antigen Binding), and a Fc fragment (crystallizable fraction). The Fc fragment is the support for the effector functions of immunoglobulins.

Using pepsin digestion, a F(ab')2 fragment is generated where both Fab fragments remain linked by two disulfide bonds, and the Fc fragment is split into several peptides. The F(ab')2 fragment is formed by two Fab' fragments (one Fab' fragment consisting of a Fab and a hinge region), linked by intercatenary disulfide bonds in order to form a F(ab')2.

Such fragments, which contain the binding site of the antibody, may have lost some of the properties of a whole antibody from which they are derived, such as the ability to activate the complement or to bind the Fcgamma receptors. However, these fragments have not lost the ability of the whole antibody to neutralize the inhibitor antibody. Thus, the invention refers also to the F(ab')2, Fab', Fab fragments, or to the CDR region or any modified version of any of these fragments or region of the antibody 18B6. Particularly, these fragments have preserved the ability of the whole antibody to neutralize RHD5 antibodies.

A further aspect of the invention is a stable cell line producing an antibody such as described above. The stable cell line of the invention can be of human or animal origin. The stable cell line of the invention can originate from human immortalized cells. In a further embodiment of the invention, this cell line can originate from immortalized cells of animal origin, for example mice. A preferred example of a cell line obtained in this embodiment of the invention is the line 18B6, deposited at CNCM under the number 1-3559. In a further embodiment, the stable cell line of the invention is a line which has integrated a genetic construction allowing the expression of the antibody of the invention at the desired point of the genome. The step consisting of obtaining such a cell is a stable transfection. This step can be applied to any type of cells as long as they can be maintained in in vitro culture. Stable transfection requires integration of the genetic construction, which can be carried out by homologous recombination or randomly. The presence of a positive selection cassette in the genetic construction comprising the gene of interest which confers antibiotic resistance to the cell, for example, attests to the insertion of the transgene into the cell genome. As result of a sub-cloning step, a long term producer cell line is obtained from the antibody of the invention, for example 18B6, which can be maintained in in vitro culture.

The stable cell line expressing an antibody of the invention can be selected from the group consisting of a human cell line, a rodent cell line, for example a mouse cell line, SP2/0, YB2/0, IR983F, a human myeloma such as Namalwa, or any other cell of human origin such as PERC6, CHO cell lines, namely CHO-K-1, CHO-Lec10, CHO-Lec1, CHO-Lec13, CHO Pro-5, CHO dhfr-(CHO DX B11, CHO DG44), or further cell lines selected from Wil-2, Jurkat, Vero, Molt-4, COS-7, 293-HEK, BHK, K6H6, NS0, SP2/0-Ag 14 and P3X63Ag8.653.

A further particular subject matter of the invention is the hybridoma 18B6 deposited under the registration number CNCM I-3559 at the Collection Nationale de Cultures de Microorganismes (CNCM). The variable region of each of the light chains of the monoclonal anti-idiotypic antibody produced by the hybridoma 18B6 is coded by the nucleic acid sequence SEQ ID NO: 16, and the variable region of each of the heavy chains of the monoclonal anti-idiotypic antibody produced by the hybridoma 18B6 is coded by the nucleic acid sequence SEQ ID NO: 15. The antibody produced by the hybridoma 18B6 is the antibody 18B6, and a method for obtaining the hybridoma 18B6 is described in the "Examples" Section of the present document.

A further subject matter of the invention is a DNA fragment of the sequence SEQ ID NO: 15 encoding the variable region of the heavy chain of the antibody of the invention such as previously described. This DNA fragment can be inserted into a vector enabling the expression of a polypeptide, preferably of an antibody, the variable region of the heavy chain of said antibody is coded by the nucleic acid sequence SEQ ID NO: 15, the derived peptide sequence of which is the sequence SEQ ID NO: 17, in order to be introduced and maintained in a host cell. This vector enables the expression of this foreign nucleic acid fragment in the host cell because it contains the sequences (promoter, polyadenylation sequence, selection gene) essential for this expression. Such vectors are well known to those skilled in the art, and can be an adenovirus, a retrovirus, a plasmid or a bacteriophage, this list is not being limitative. In addition, any mammalian cell can be used as the host cell, that is as the cell expressing the polypeptide or the antibody of the invention, for example SP2/0, YB2/0, IR983F, a human myeloma such as Namalwa, or any other cell of human origin such as PERC6, CHO cell lines, namely CHO-K-1, CHO-Lec10, CHO-Lec1 CHO-Lec13, CHO Pro-5, CHO dhfr-(CHO DX B11, CHO DG44), or other lines selected from Wil-2, Jurkat, Vero, Molt-4, COS-7, 293-HEK, BHK, K6H6, NS0, SP2/0-Ag 14 and P3X63Ag8.653.

A further aspect of the invention is a DNA fragment of the sequence SEQ ID NO: 16 coding the variable region of the light chain of an antibody of the invention such as previously described. This DNA fragment can be inserted into a vector enabling the expression of a polypeptide, preferably of an antibody, the variable region of the light chain of said antibody is coded by the nucleic acid sequence SEQ ID NO: 16, the deduced peptide sequence thereof is the sequence SEQ ID NO: 18, in order to be introduced into and maintained in a host cell. This vector enables the expression of this foreign nucleic acid fragment in the host cell because it contains the sequences (promoter, polyadenylation sequence, selection gene) essential for this expression. Such vectors are well known to those skilled in the art, and can be an adenovirus, a retrovirus, a plasmide or a bacteriophage, this list not being limitative. In addition, any mammalian cell can be used as host cell, that is as the cell expressing the polypeptide or the antibody of the invention, for example SP2/0, YB2/0, IR983F, a human myeloma as Namalwa, or any other cell of human origin as PERC6, CHO cell lines, especially CHO-K-1, CHO-Lec10, CHO-Lec1, CHO-Lec13, CHO Pro-5, CHO dhfr-(CHO DX B11, CHO DG44), or other lines selected from Wil-2, Jurkat, Vero, Molt-4, COS-7, 293-HEK, BHK, K6H6, NS0, SP2/0-Ag 14 and P3X63Ag8.653.

A further aspect of the invention is a pharmaceutical composition comprising an antibody of the invention and at least an excipient and/or at least one pharmaceutically acceptable carrier. Preferably, the monoclonal anti-idiotypic antibody contained in the pharmaceutical composition of the invention is the antibody 18B6, a fragment or a region derived from 18B6, or even a chimeric or humanized antibody comprising the variable regions or the CDRs of 18B6, and such as previously described in the present document. The pharmaceutical composition of the invention can be formulated into any excipient which can be tolerated by a patient to be treated. Examples of such excipients include water, saline solutions, Ringer's solution, dextrose solutions, and any other suitable aqueous physiological solution. The excipient can also contain low amounts of additives, such as substances increasing the isotonicity and the stability of the composition. Such excipients include phosphate buffer, bicarbonate buffer, and Tris buffer. Such excipients are well known to those skilled in the art. Standard formulations can be in the form of liquids for injection or solid formulations which can be resuspended in a suitable liquid prior to administration. The useful carriers for preparing the pharmaceutical composition of the invention advantageously have the function of increasing the half-life of the therapeutic composition in the animal or patient, or enabling the controlled release of the active ingredient. Such carriers can be organic and synthetic polymers and further chemical compounds capable of disseminating the medicaments at a normal rate or disseminating them only in certain environments, and can also be liposomes, this list being not limitative.

Advantageously, the pharmaceutical composition of the invention, moreover, comprises at least an anti-idiotypic antibody directed against the inhibitory antibody binding to a domain different from the C1 domain of Factor VIII. This other antibody can be an anti-idiotypic antibody directed against an inhibitor antibody binding to the A1, or A3, or B, A2 or C2 domains of Factor VIII. Indeed, a patient suffering from haemophilia A, having developed inhibitory antibodies, exhibits most frequently several types of inhibitory antibodies. In addition, the amounts and the nature of the different types of inhibitory antibodies are not fixed but may change during the patient's life. The different inhibitory antibodies of a same patient are thus directed against the different domains of Factor VIII, and it is particularly advantageous to treat the patient not with one but with several types of anti-idiotypic antibody, directed against the different inhibitory antibodies.

Preferably, the pharmaceutical composition comprises a monoclonal anti-idiotypic antibody directed against an inhibitory antibody binding to the C2 domain of Factor VIII and/or an inhibitory antibody binding to the A2 domain of Factor VIII, and the monoclonal antibody of the invention. Indeed, the A2 and C2 domains are the main targets of the anti-Factor VIII immune reaction. Thus, a pharmaceutical composition comprising a mixture of anti-idiotypic antibodies directed against inhibitory antibodies binding to the C1 domain of Factor VIII and of anti-idiotypic antibodies directed against inhibitory antibodies binding to the C2 domain, enables neutralization of at least 70%, and advantageously at least 80% or 90% of all inhibitory antibodies present in a patient. In a preferred embodiment of the invention, the pharmaceutical composition of the invention comprises the antibody 14C12 (deposited under the number LMBP 5878CB at the Belgian Coordinated Collections of Microorganisms) and/or the antibody 30D1 (deposited at CNCM under the number 1-3450). In a further preferred embodiment of the invention, the pharmaceutical composition comprises the chimeric antibody 14C12 deposited at the CNCM under the number 1-3510 and/or a chimeric or humanized antibody derived from the antibody 30D1, that is an antibody comprising the variable regions of the antibody 30D1.

A further aspect of the invention is the use of the antibody of the invention as a medicament.

A further aspect of the invention is the use of the antibody of the invention for manufacturing a medicament. Advantageously, such a medicament is used for reducing and/or preventing and/or treating bleeding in a patient suffering from haemophilia comprising inhibitory antibodies directed against the C1 domain of Factor VIII.

A further aspect of the invention is the use of the antibody of the invention for manufacturing a medicament intended for the treatment of type A haemophilia.

Advantageously, the thus treated type A haemophilia is a haemophilia with inhibitors. This type of haemophilia treated with the antibody of the invention can be inborn or acquired. By neutralizing the inhibitory antibodies, the antibody of the invention makes treatment by injection of Factor VIII to a patient effective, since the activity of Factor VIII is no longer inhibited by inhibitory antibodies.

A further aspect of the invention is the use of the antibody of the invention for neutralisation of the in vitro or in vivo inhibitory activity of an inhibitory antibody directed against the C1 domain of Factor VIII. This process can be carried out in order to deplete the inhibitory antibodies directed against the C1 domain of Factor VIII from the blood of a patient, and afterwards to re-inject the treated blood to said patient.

A further aspect of the invention is related to a medicament comprising an antibody of the invention, preferentially the antibody 18B6.

A further aspect of the invention is the use of the antibody for adsorption of the inhibitory antibodies, by way of example in order to purify Factor VIII inhibitory antibodies.

Finally, a further aspect of the invention is the use of the antibody of the invention for detection and/or purification of Factor VIII inhibitory antibodies. The general processes carrying out such methods of detection and purification are well known to those skilled in the art. By way of example, the use of an immuno-purification column containing beads with the antibody of the invention grafted on their surface, can be mentioned. Only the molecules recognized by the antibody will affix themselves to the beads. The others will pass through the column. In order to recover the molecule, an increase of the ionic strength of the solvent is sufficient.

Further aspects and advantages of the invention will be described in the following examples, which are to be considered by way of illustration and not of limitation to the scope of the invention.

EXAMPLES

Example 1

Production of a Human Monoclonal Antibody Directed Against the C1 Domain of Factor VIII («Anti-C1 Antibody»)

The human lymphoblastoid cell line RHD5 described here below was obtained by immortalization of B lymphocytes of a patient suffering from acquired haemophilia A having developed an immune response to Factor VIII, according to the procedure described in the document Jacquemin et al. (1998), Blood 92, 496-506 and in the patent application WO 2005/016455.

The cell line producing the monoclonal anti-C1 RHD5 antibody was deposited at the Belgian Co-ordinated Collections of Microorganisms/Plasmid Collection (BCCM/LMBP), Laboratorium voor Moleculaire Biologie, University of Ghent, Technologiepark 297, B-9052 Zwijnaarede, Belgium, in August 2004, by the Collen Research Foundation, under the accession number LMBP 6165CB.

The nucleotide sequence of the variable region of the heavy chain of the RHD5 antibody is sequence SEQ ID NO: 5, the latter having the following nucleic acid sequence:

```
atggactgga cctggaggtt cctctttgtg gtggcagcag ctgcaggtgt ccagtcccag gtgcagctgg tgcagtctgg ggctgaggtg aagaagcccg ggtcgtcggt gatggtctcc tgcaaggctt ctggaggcac cttcagcagc tttggtatca
```

```
gctgggtgcg acaggcccct ggacaagggc ttgagtgggt gggagggatc atccctatct ttggtacagc aaacaccgca cggaacttcc agaatagagt caccattacc gcggacgaat tcacgagcac agcctacata cgactgagga gcctgagatc tgaagatacg gccgtgtatt actgtgtcgg cggtcgagat gcctacagct ttgatggttt tgatgtctgg ggccaaggga caatggtcac cgtctcttca g,
``` and the nucleotide sequence of the variable region of the light chain of the RHD5 antibody is sequence SEQ ID NO: 6, the latter having the following nucleic acid sequence:

```
atggcatgga tccctctctt cctcggcgtc cttgtttact gcacaggatc cgtggcctcc tctgggctga ctcagccaca ctcagtgtcc gtgtcccag gacagacagc caacatcacc tgctctagag ataagttggg tcataaattt gcttcctggt atcaacagaa gccaggccag tccctgctc ttctcatcta tcaagacagc aagcggccct cagggatccc tgagcgattc tctggctcca actctgggaa cacagccact ctgaccatca gcgggaccca ggctatggat gaggctgact attactgtca ggcgtgggac aacaccactg ccgtattcgg cggagggacc aagttgacag tcctaagtca gccca.
```

The peptide sequence corresponding to the sequence SEQ ID NO: 5 is sequence SEQ ID NO: 7, the latter having the following amino acid sequence:

```
Met Asp Trp Thr Trp Arg Phe Leu Phe Val Val Ala

Ala Ala Ala Gly Val Gln Ser Gln Val Gln Leu Val

Gln Ser Gly Ala Glu Val Lys Lys Pro Gly Ser Ser

Val Met Val Ser Cys Lys Ala Ser Gly Gly Thr Phe

Ser Ser Phe Gly Ile Ser Trp Val Arg Gln Ala Pro

Gly Gln Gly Leu Glu Trp Val Gly Gly Ile Ile Pro

Ile Phe Gly Thr Ala Asn Thr Ala Arg Asn Phe Gln

Asn Arg Val Thr Ile Thr Ala Asp Glu Phe Thr Ser

Thr Ala Tyr Ile Arg Leu Arg Ser Leu Arg Ser Glu

Asp Thr Ala Val Tyr Tyr Cys Val Gly Gly Arg Asp

Ala Tyr Ser Phe Asp Gly Phe Asp Val Trp Gly Gln

Gly Thr Met Val Thr Val Ser Ser,
``` and the peptide sequence corresponding to the sequence SEQ ID NO: 6 is sequence SEQ ID NO: 8, the latter having the following amino acid sequence:

```
Met Ala Trp Ile Pro Leu Phe Leu Gly Val Leu Val

Tyr Cys Thr Gly Ser Val Ala Ser Ser Gly Leu Thr

Gln Pro His Ser Val Ser Val Ser Pro Gly Gln Thr

Ala Asn Ile Thr Cys Ser Arg Asp Lys Leu Gly His

Lys Phe Ala Ser Trp Tyr Gln Gln Lys Pro Gly Gln

Ser Pro Ala Leu Leu Ile Tyr Gln Asp Ser Lys Arg

Pro Ser Gly Ile Pro Glu Arg Phe Ser Gly Ser Asn

Ser Gly Asn Thr Ala Thr Leu Thr Ile Ser Gly Thr

Gln Ala Met Asp Glu Ala Asp Tyr Tyr Cys Gln Ala

Trp Asp Asn Thr Thr Ala Val Phe Gly Gly Gly Thr

Lys Leu Thr Val Leu Ser Gln Pro.
```

Optionally, antibodies exhibiting the required properties can be produced by immunization of animals. In this case, human Factor VIII is injected into mice with an adjuvant. Monoclonal anti-human antibodies are obtained by fusion of spleen lymphocytes with a mouse myeloma cell line. Cell supernatants producing the anti-Factor VIII antibodies are identified and cloned by limiting dilution. A general description of such methods can be found in <<Current Protocols in Immunology, Chapter 2, John Wiley & Sons, Inc, 1994>>. Further selections of inhibitors exhibiting the desired properties are described hereafter.

Example 2

Production of Anti-Idiotypic Antibody 18B6

I. Mice Immunization

Four 6 week old Balb/c female mice were sub-cutaneously injected (SC) thrice in the footpad, with 10 µg of the human anti-C1 domain of FVIII RHD5 antibody suspended in a complete Freund's adjuvant (ACF) (1st immunization) then in an incomplete Freund's adjuvant (AIF).

The first bloodletting (bloodletting 0) was performed prior to immunization (bleeding Day 0 (D0)), then the injections and bloodletting proceeded as follows:

D1: Injection N°1 (10 µg of RHD5 antibody in the presence of complete Freund's adjuvant)

D15: Bloodletting N°1

D16: Injection N°2 (10 µg of RHD5 antibody in the presence of incomplete Freund's adjuvant)

D28: Bloodletting N°2

D29: Injection N°3 (10 µg of RHD5 antibody in the presence of incomplete Freund's adjuvant)

D44: Bloodletting N°3

II. Evaluation of the Immune Response of Mice

In order to evaluate the presence of the anti-RHD5 antibodies in the different bloodlettings, an ELISA assay with direct binding is performed. To this end, either the RHD5 antibody, or a control IgG1 at 3 µg/ml were insolubilized, 50 µl/well, un Glycine buffer, over night at 4° C. (Glycine buffer=0.1M Glycine, 0.17M NaCl, pH 9.2). Three washings are performed with PBS/Tween (PBS=140.0 mM NaCl, 2.6 mM KCl, 1.4 mM $KH_2PO_4$, 8.1 nM $Na_2HPO_4.2H_2O$, pH 7.4). The system is left at saturation for 30 minutes at room temperature (RT) with 100 µl/well of Magic Buffer (Magic Buffer=50 mM Tris, 0.17M NaCl, 1% BSA, pH 7.2). Afterwards, the bloodlettings were diluted to 1/10, 1/100, 1/1000 and 1/10000 in Magic Buffer and incubated for 2 hours at room temperature (50 µl/well). Then, 3 washings are carried out in PBS/Tween. Subsequently, the system is incubated with a 1 µg/ml solution of goat polyclonal mouse anti-IgG antibodies labelled with HRP (horseradish peroxidase) (Bio-Rad) for 2 hours at room temperature (50 μl/well) (dilution in Magic Buffer). Then, the system is washed 3 times with PBS/Tween, and revelation is carried out with a chromogen (Ortho-phenyl diamine) and the intensity of the obtained coloration is read using a reader with filters corresponding to wavelengths 490/650 nm (reader Emax Molecular Devithese, Sunnyvale, Calif.).

Result of Optical Densities Obtained with the Control IgG1:

TABLE 1

| Dilution 1000X | Mouse 1 | Mouse 2 | Mouse 3 | Mouse 4 |
|---|---|---|---|---|
| Bloodletting 0 | 0.031 | 0.019 | 0.018 | 0.018 |
| Bloodletting 1 | 0.019 | 0.020 | 0.025 | 0.028 |
| Bloodletting 2 | 0.026 | 0.023 | 0.169 | 0.045 |
| Bloodletting 3 | 0.027 | 0.063 | 0.150 | 0.024 |

Result of Optical Densities Obtained with RHD5:

TABLE 2

| Dilution 1000X | Mouse 1 | Mouse 2 | Mouse 3 | Mouse 4 |
|---|---|---|---|---|
| Bloodletting 0 | 0.047 | 0.020 | 0.012 | 0.018 |
| Bloodletting 1 | 0.446 | 0.188 | 0.142 | 0.157 |
| Bloodletting 2 | 0.632 | 0.685 | 0.648 | 0.911 |
| Bloodletting 3 | 0.570 | 0.708 | 0.778 | 0.852 |

The results obtained are depicted in FIG. 1.

Conclusion: Each mouse responded correctly and reacted similarly to the injection of the RHD5 Fab fragment. In an arbitrary manner, mouse n°4 was selected to carry out the fusion.

III. Fusion and Screening

The fusion of spleen lymphocytes of mouse n°4 with cells of a myeloma SP2/0 was carried out. The fusion was carried out in a conventional way for those skilled in the art (J. G. Gilles et al., Blood (2004) 103: 2617-23; P. Cornelis, <<Les anticorps monoclonaux>>, Revue IRE, vol. 7, N°4, 1983).

The cells were successively expanded in a DMEM medium (Dulbecco's Modified Eagle Medium) containing hypoxanthine and thymidine according to the principle of limit dilutions and the clones tested positive detected in direct binding ELISA assay, such as previously described in point II.

The specificity of the binding was confirmed by insolubilizing a human IgG1 antibody having an irrelevant specificity, and produced in the Laboratory.

In order to determine hybridoma stability, the epitope screening tests (tests 1 to 3) were repeated during clones expansion, in different volumes of medium from 200 μl to 5 ml.

Test 1=measurement in well of 200 μl
Test 2=measurement in well of 1 ml
Test 3=measurement in bottle of 5 ml Results obtained during different epitope screenings are resumed in the following Table:

TABLE 3

| | Screening 1 | Screening 2 | Screening 3 | Screening 3/ IgG1 | Inhibition: Elisa | Neutralization: functional test |
|---|---|---|---|---|---|---|
| 1A1 | + | − | − | − | | |
| 1F3 | + | + | + | − | +(92.5%) | +(100%) |
| 2A1 | + | − | − | − | | |
| 2C9 | + | + | + | + | | |
| 3G9 | + | + | + | + | | |
| 4B7 | + | + | − | − | | |
| 4B10 | + | + | + | + | | |
| 4D5 | + | + | + | + | | |
| 5B11 | + | + | + | − | +(93.6%) | +(100%) |
| 5E1 | + | − | +/− | + | | |
| 5G3 | + | + | + | + | | |
| 5H7 | + | − | − | + | | |
| 5H8 | + | + | +/− | + | | |
| 6A9 | + | + | + | + | | |
| 6E1 | + | + | +/−− | + | | |
| 6H7 | + | + | + | + | | |
| 6H8 | + | + | + | + | | |
| 9D2 | + | − | − | + | | |
| 10D2 | + | + | + | − | +(93.6%) | +(100%) |
| 10G8 | + | + | + | − | − | |
| 11C5 | + | + | + | − | − | |
| 11D7 | + | − | − | − | | |
| 11G3 | + | + | + | + | | |
| 12D7 | + | + | + | − | − | |
| 12G3 | + | − | − | − | | |
| 12H12 | + | + | + | − | − | |
| 13A1 | + | + | + | − | +(90.9%) | +(95.6%) |
| 13C3 | + | + | + | − | +(93.6%) | +(100%) |
| 13D7 | + | + | + | − | | |
| 13H5 | + | + | +/− | + | | |
| 14H1 | + | + | − | − | | |
| 14D11 | + | + | +/−− | + | | |
| 14F11 | + | + | + | − | +(83.6%) | +(100%) |
| 14H2 | + | + | + | + | | |
| 14H5 | + | + | + | + | | |
| 15B4 | + | + | − | − | | |
| 15F6 | + | − | − | + | | |
| 16B4 | + | + | + | − | +(94%) | +(90.9%) |
| 16F6 | + | + | + | − | − | |

TABLE 3-continued

| | Screening 1 | Screening 2 | Screening 3 | Screening 3/ IgG1 | Inhibition: Elisa | Neutralization: functional test |
|---|---|---|---|---|---|---|
| 17A5 | + | + | + | + | | |
| 17C4 | + | + | + | − | +(92.4%) | +(100%) |
| 18A5 | + | + | + | − | − | |
| 18A9 | + | + | + | − | − | |
| 18B6 | + | + | + | − | +(93.1%) | +(100%) |
| 18C4 | + | + | + | + | | |
| 19C4 | + | + | + | + | | |
| 19G3 | + | + | − | +/− | | |
| 20A7 | + | + | + | + | | |
| 20C4 | + | − | − | − | | |
| 20G3 | + | − | − | − | | |
| 21D8 | + | + | + | − | +(93.8%) | − |
| 22H7 | + | − | + | + | | |
| 23A7 | + | + | + | − | − | |
| 23E3 | + | + | − | − | | |
| 23G2 | + | − | +/− | − | − | |
| 24D5 | + | + | + | − | +/−(56.3%) | +/−(76.9%) |
| 24D12 | + | + | + | + | | |
| 24E3 | + | − | − | − | | |
| 28C10 | + | − | − | − | | |

IV. Inhibition Assay with Culture Supernatants

As shown in Table 3, a test of inhibition was carried out with the culture supernatants. This assay was carried out in order to select, from the clones, the anti-idiotypic antibodies which exactly recognize an epitope determinant located at the paratope level of the RHD5 Ab. The anti-idiotypic antibodies were tested in an ELISA assay for inhibition of binding of the RHD5 to the insolubilized FVIII.

Recombinant Factor VIII (recFVIII) (Baxter) at 2 µg/ml in a glycine buffer, 50 µl/well, was insolubilized, then left for 2 hours at room temperature. The RHD5 antibody (or an irrelevant IgG1) at 0.6 µg/ml final concentration was pre-incubated over 2 hours with the culture supernatants in a dilution 1/1, 1/2 and 1/4 in Magic Buffer. The wells were washed 3 times with a PBS/Tween buffer, then saturated with 100 µl/well of Magic Buffer (30 min at room temperature). Afterwards, the culture supernatant was incubated with 50 µl of RHD5 (or irrelevant IgG1) (2 hours at room temperature, Magic Buffer), then, 3 washings were performed. The RHD5 antibodies bound to insolubilized recFVIII were detected by addition of 50 µl/well of a mouse polyclonal human anti-IgG HRP-labelled (Southern Biotechnology) antibodies solution of 1 µg/ml in Magic Buffer. Three successive washings were carried out with PBS/Tween, then revelation carried out with a chromogen (OPD ortho-phenyl diamine) and a reading of the obtained coloration intensity with a reader having filters corresponding to wavelengths 490/650 nm (reader Emax Molecular Devithese, Sunnyvale, Calif.).

Conclusions:

As shown in Table 3, 11 clones are able to specifically inhibit the RHD5 antibody binding to insolubilized recFVIII. (N.B.: A negative value either expresses the possibility of binding to an external region of the paratope, or reflects an insufficient concentration of the Ab in the culture supernatant. However, with respect to the number of positives, the negative wells were eliminated from the following tests).

V. Functional Test with Culture Supernatants: Measurement of Neutralisation of RHD5 Antibody Inhibitory Activity (Anti-Factor VIII)

The RHD5 antibody is incubated at a concentration of 1 µg/ml with supernatants of different clones selected during the test of inhibition (diluted 3 times, 6 times, 12 times and 24 times) in Magic Buffer at 37° C. After 30 min, the FVIII Kogenate (Bayer) at 0.5 U/ml final was added, then a complementary incubation of 30 min at 37° C. was carried out. The samples were diluted 30× in Magic Buffer, then the reagents of the chromogenic DADE test (Factor VIII chromogenic, Dade Behring Gmbh, Marburg, Germany) were added following the manufacturer's instructions.

As shown in the Table 3, 10 clones are able to neutralize the inhibitory activity of the RHD5 Ab. Antibody 18B6 was selected to be used in the following experiences, as a function of the results and neutralisation curves.

VI. Extensive Production of the Selected 18B6 Anti-RHD5 Clone

The anti-idiotypic antibody 18B6 was produced in a DMEM culture medium. This production was followed by purification on a Protein G affinity column (which enables purification, then concentration of the antibodies, and thus to ascertain further the obtained anti-idiotypic antibody specificity).

Purification: 18B6: production of 8 ml at 8.48 mg/ml

VII. Specificity Evaluation

The various preparations were evaluated with an ELISA following the same protocol as described in points II. and IV.

ELISA assay: direct binding of the anti-idiotypic antibody 18B6 to insolubilized antibody RHD5

Figure 2:
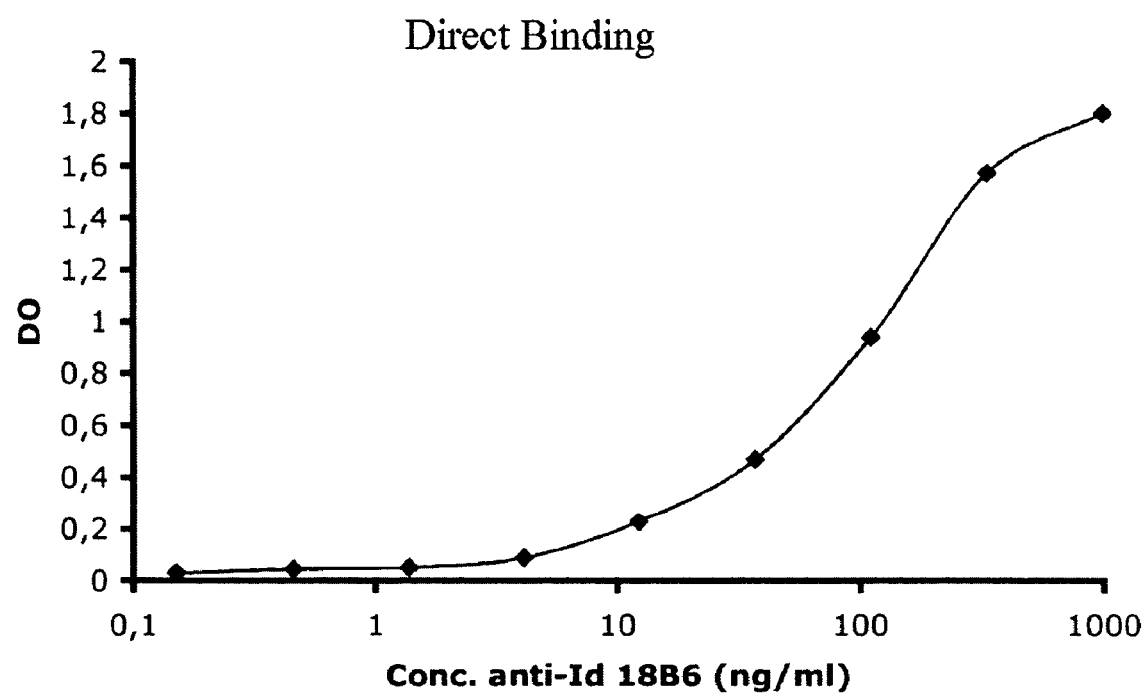
FIG. 2: direct binding of the anti-idiotypic antibody 18B6 to the insolubilized antibody RHD5.

The direct binding of the anti-idiotypic antibody 18B6 to the insolubilized antibody RHD5 is illustrated in FIG. 2. The curve shows that the binding of antibody 18B6 to RHD5 is dose-dependent.

ELISA assay: inhibition of antibody RHD5 binding to insolubilized recombinant FVIII.

The inhibition of RHD5 antibody binding to insolubilized recombinant FVIII was measured according to the protocol described in point IV. The concentration of used RHD5 is equal to 2 µg/ml.

TABLE 4

| Conc. 18B6 µg/ml | Inhibition of binding (%) |
|---|---|
| 50 | 96.1 |
| 25 | 97.2 |
| 12.5 | 96.9 |
| 6.25 | 96.7 |
| 3.12 | 94.1 |
| 1.56 | 90.3 |

TABLE 4-continued

| Conc. 18B6 µg/ml | Inhibition of binding (%) |
|---|---|
| 0.78 | 50.3 |
| 0.39 | 9.2 |
| 0.195 | 0 |
| 0.098 | 0 |

Figure 3:
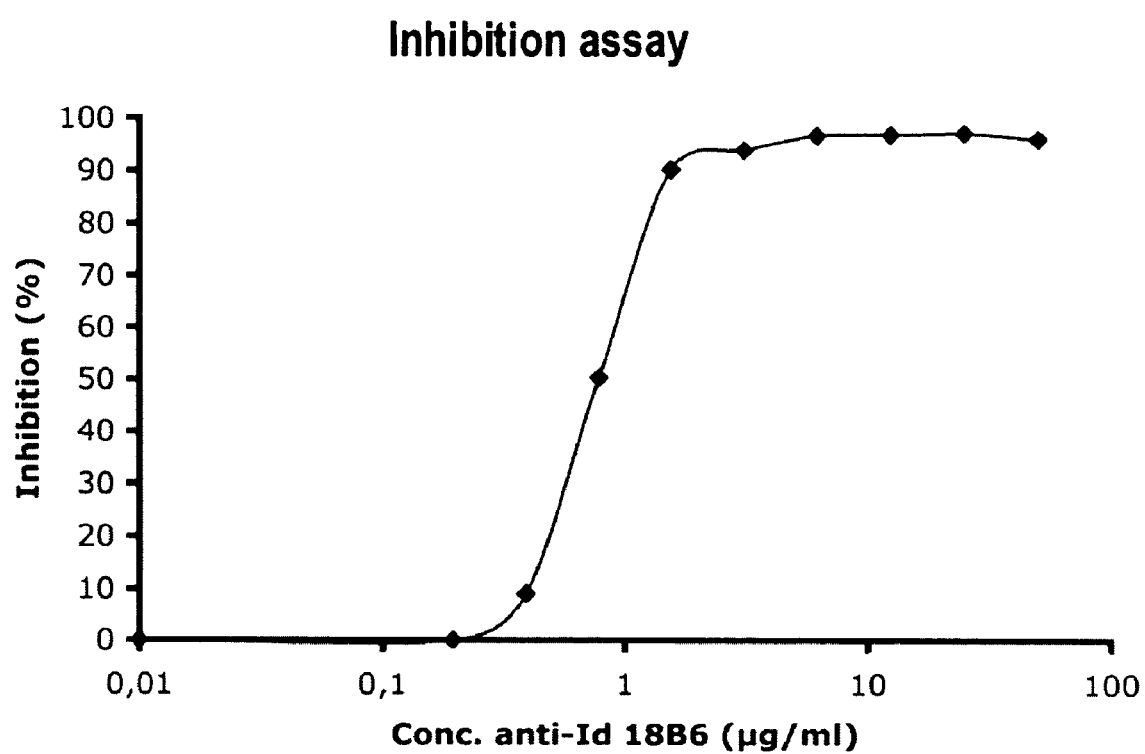
FIG. 3: inhibition of the binding of the antibody RHD5 to insolubilized recombinant FVIII (recFVIII)

The results are shown in FIG. 3. A 50% inhibition of RHD5 binding to FVIII is obtained at a molar ratio RHD5/18B6 of 2.5, while an equimolar ratio inhibits 92% of this binding.

3. Functional Test: Measurement of the Neutralisation of RHD5 Antibody Inhibitory Activity (Anti-FVIII)

The protocol is the same as described in point V with a final RHD5 concentration of 0.4 µg/ml and a curve of purified anti-idiotypic antibody from 4 to 0.002 µg/ml final concentration.

The results are given in the following Table 5:

TABLE 5

| Conc. anti-Id (µg/ml) | Neutralisation (%) |
|---|---|
| 4 | 89.5 |
| 1.33 | 81.2 |
| 0.44 | 54.3 |
| 0.148 | 27.4 |
| 0.049 | 11 |
| 0.0165 | 8.8 |
| 0.0055 | 6.7 |
| 0.00183 | 8.9 |
| 0.0006 | 6.7 |
| 0.0002 | 0 |

Figure 4:
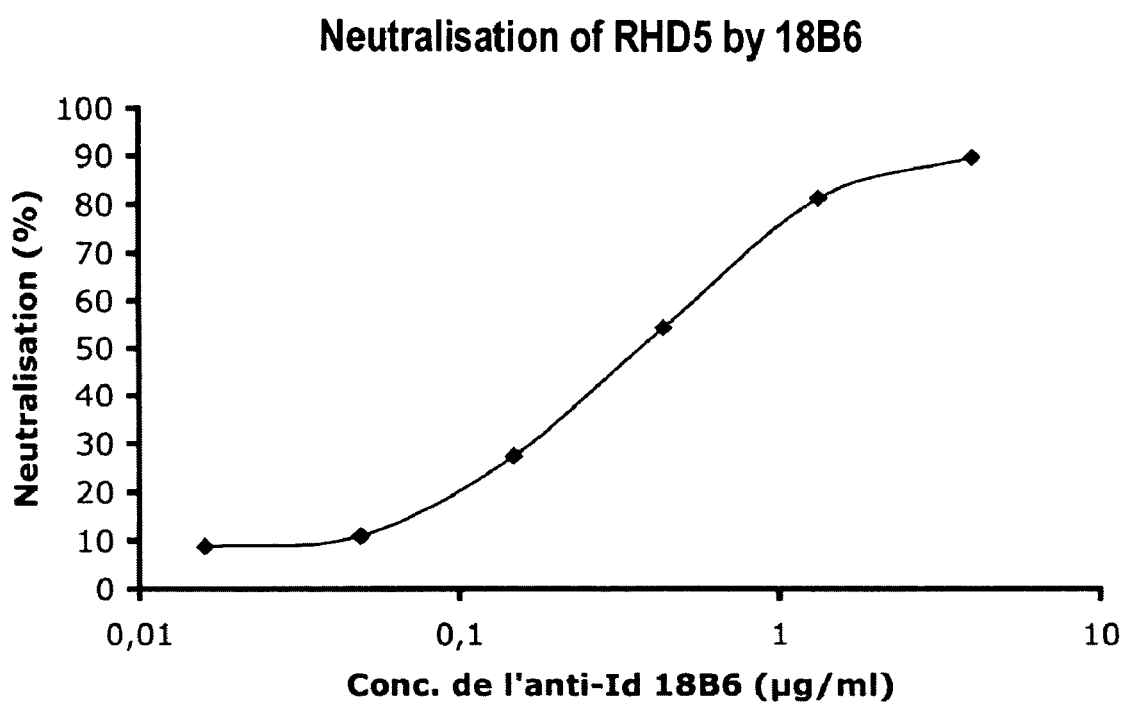
FIG. 4: neutralisation of RHD5 by 18B6. .

The results are illustrated in FIG. 4. A 50% neutralisation of RHD5 inhibitory activity is obtained at an equimolar RHD5/18B6 ratio.

4. Measurement of the Binding Kinetics of Anti-Idiotypic Antibody 18B6 with the <<Surface Plasmon Resonance Biacor>> Method The binding kinetics of the anti-idiotypic antibody 18B6 to inhibitor RHD5 antibody was evaluated by use of the <<Surface plasmon resonance Biacore>> method using the Pharmacia Biosensor BIAcore (Pharmacia Biosensor AB, Uppsala, Sweden). The RHD5 antibodies were immobilized on the activated surface of a CM5 probe. The anti-idiotypic antibodies 18B6 were infused in different RHD5 concentrations immobilized on the surface of the probe. The association and dissociation constants were determined:

$K_a(M-1S-1) = 4.26 \times 10^3$ $K_d(S-1) = 1.45 \times 10^{-5}$ $K_D: M \cdot 3.4 \times 10^{-9}$ 5. Characterization of the Anti-Idiotypic Antibody 18B6 Sub-Class In order to determine the sub-class of the antibody 18B6, the IsoStrip system by Roche was used (colorimetric strip). The antibody 18B6 was identified as a IgG1 Kappa.

VIII. Sequence of the Antibody 18B6

In order to carry out sequencing, mRNA of hybridoma producing the anti-idiotypic antibody 18B6 was isolated, using a Quick Prep Micro mRNA Purification Kit (Amersham Pharmacia Biotech, Uppsala, Sweden). The cDNA was synthesized by use of First-strand cDNA Synthesis Kit (Amersham Pharmacia Biotech). The cDNA encoding the heavy chain (VH) and the light chain (VL) was amplified by PCR (Polymerase Chain Reaction) using specific primers corresponding to different families of genes potentially found in the mouse. The PCR products were isolated from an agarose gel 1.5% by means of QIA quick Gel Extraction Kit (Qiagen, Hilden, Germany) and cloned with pGEM-T Easy Vector system (Promega, Madison, Wis.). Plasmidic DNA of positive colonies was isolated by means of High Pure Plasmid Isolation Kit (Roche Diagnostics, Mannheim, Germany) and sequenced in both directions with Seqenase (US Biochemical, Cleveland, Ohio).

IX. Particular Properties of the 18B6 Antibody

Antibody 18B6 completely inhibits RHD5 antibody binding to its antigen, Factor VIII. The RHD5 antibody carries an idiotype complementary to that of 18B6.

The binding of an antibody to the antigen involves an interface of mutual recognition of 6 to 12 angströms$^2$ corresponding to a great number of amino acids which associate one with another by hydrogen bonds, hydrophobic or polar attraction and VanderWals bridges.

At a functional level, when an antibody completely inhibits the binding of an antibody to the antigen, this implies that the inhibiting antibody carries an "internal image" of the antigen, that is, a three-dimensional structure mimicking the 3-D structure of the antigen.

Although the primary structure (amino acids sequence) of the 18B6 antibody shows low identity to the C1 domain of Factor VIII, the alignment of secondary structures of the 18B6 antibody with that of the C1 domain of FVIII, the antigenic target of the RHD5 antibody, and three-dimensional modelling of the 18B6 indicate, by superposition with the 3-D structure of the C1 domain, that the variable part of the light chain (VL) of 18B6 represents an internal image of the C1 domain.

This observation confers on the 18B6 antibody a particular, novel and not foreseeable property. In other words, any attempt to generate antibodies similar to 18B6 by immunization with an antibody such as RHD5 does not yield de facto antibodies identical to 18B6.

While the invention has been described in detail with reference to preferred embodiments thereof, it will be apparent to one skilled in the art that various changes can made made, and equivalents employed, without departing from the scope of the invention. Each of the aforementioned documents is incorporated by reference herein in their entireties.

The invention claimed is:

1. A monoclonal anti-idiotypic antibody directed against the Factor VIII human inhibitory antibody RHD5, said inhibitory antibody being deposited at the collection BCCM/LMBP under the number LMBP 6165CB, and said inhibitory antibody being directed against the C1 domain of Factor VIII, wherein the variable region of each of the light chains of said monoclonal anti-idiotypic antibody is coded by the nucleic acid sequence SEQ ID NO: 16, and the variable region of each of the heavy chains of said monoclonal anti-idiotypic antibody is coded by the nucleic acid sequence SEQ ID NO: 15.

2. The monoclonal anti-idiotypic antibody according to claim 1, wherein the peptide sequence deduced from the sequence SEQ ID NO: 16 is the sequence SEQ ID NO: 18 and in that the peptide sequence deduced from the sequence SEQ ID NO: 15 is the sequence SEQ ID NO: 17.

3. The monoclonal anti-idiotypic antibody according to claim 1, wherein said monoclonal anti-idiotypic antibody is a mouse antibody.

4. The monoclonal anti-idiotypic antibody according claim 3, wherein said monoclonal anti-idiotypic antibody is a IgG1kappa.

5. The monoclonal anti-idiotypic antibody according to claim 1, wherein said monoclonal anti-idiotypic antibody is a chimeric antibody.

6. The monoclonal anti-idiotypic antibody according to claim 5, wherein said monoclonal anti-idiotypic antibody is a human hybrid antibody.

7. The monoclonal anti-idiotypic antibody according to claim 4, wherein the monoclonal anti-idiotypic antibody is selected from the group consisting of a F(ab')2 fragment, a Fab' fragment, and a Fab fragment of the monoclonal anti-idiotypic antibody.

8. The monoclonal anti-idiotypic antibody according to claim 1, which is capable of being produced by the hybridoma 18B6, and is deposited under registration number CNCM 1-3559 at the Collection Nationale de Cultures de Microorganismes (CNCM).

9. A stable cell line producing the monoclonal anti-idiotypic antibody according to claim 1.

10. The stable cell line according to claim 9, selected from the group consisting of: SP2/0, YB2/0, IR983F, the human myeloma Namalwa, PERC6, the cell lines CHO, namely CHO-K-1, CHO-Lec10, CHO-Lec1, CHO-Lec13, CHO Pro-5, CHO dhfr-, Wil-2, Jurkat, Vero, Molt-4, COS-7, 293-HEK, BHK, K6H6, NS0, SP2/0-Ag 14 and P3X63Ag8.653.

11. The hybridoma 18B6 deposited under the registration number CNCM 1-3559 at the Collection Nationale de Cultures de Microorganismes (CNCM).

12. A monoclonal anti-idiotypic antibody directed against the Factor VIII human inhibitory antibody RHD5 said inhibitor antibody being deposited at the collection BCCM/LMBP under the number LMBO 6165CB, and said inhibitory antibody being directed against the C1 domain of Factor VIII, wherein said monoclonal anti-idiotypic antibody is produced by the hybridoma 18B6 deposited under the registration number CNCM 1-3559 at the Collection Nationale de Cultures de Microorganismes (CNCM).

13. A pharmaceutical composition comprising an antibody according to claim 1 and at least one excipient and/or at least one pharmaceutically acceptable carrier.

14. The composition according to claim 13, characterized in that it comprises at least one anti-idiotypic antibody directed against an anti-FVIII antibody directed against a domain different from the C1 domain of Factor VIII.

15. The composition according to claim 13, wherein it comprises an anti-idiotypic antibody directed against an anti-FVIII antibody directed against the C2 domain of Factor VIII and/or an antibody directed against the A2 domain of Factor VIII.

16. A medicament comprising the monoclonal anti-idiotypic antibody according to claim 1.

* * * * *